United States Patent [19]

Yu

[11] Patent Number: 4,845,276

[45] Date of Patent: Jul. 4, 1989

[54] PREPARATION OF DIALKOXYBENZOIC ACID

[75] Inventor: Lin-Chen Yu, Allison Park, Pa.

[73] Assignee: Mine Safety Appliances Company, Pittsburgh, Pa.

[21] Appl. No.: 234,533

[22] Filed: Aug. 22, 1988

[51] Int. Cl.$^4$ .............................................. C07C 51/15
[52] U.S. Cl. ..................................... 562/423; 562/473
[58] Field of Search ................................ 562/423, 473

[56] References Cited

U.S. PATENT DOCUMENTS 2,816,918 12/1957 Wynkoop et al. ................... 562/423
4,590,291 5/1986 Böshagen et al. ................... 562/473
4,730,083 3/1988 Pastor et al. ......................... 562/423

FOREIGN PATENT DOCUMENTS 661555 6/1938 Fed. Rep. of Germany .
0104034 6/1985 Japan .
2010043 1/1987 Japan .

Primary Examiner—Paul J. Killos

[57] ABSTRACT 2,6-dialkoxybenzoic acid is made by metalation of 1,3-dialkoxybenzene by reaction with potassium dialkylamide. The metalated dialkoxybenzene is carbonated and acidified to form the dialkoxybenzoic acid.

3 Claims, No Drawings

PREPARATION OF DIALKOXYBENZOIC ACID

This invention relates to the preparation of dialkoxybenzoic acid and more particularly to their preparation by direct metalation of 1,3-dialkoxybenzene by reaction with potassium dialkylamide.

BACKGROUND OF THE INVENTION

Dialkoxybenzoic acids have been prepared by metalation of 1,3-dialkoxybenzene acid with butyl lithium, Chem. Abstracts 95:132423m; butyl lithium and ethyl lithium, U.S. Pat. No. 4,399,078; t-butyl sodium, Chem Abstracts 86:42548r; and phenyl sodium, Japanese Published Application No. 68 22,969 (Chem Abst. 70:77600y). These procedures first form the metal organic reactant and then metalate the dialkoxybenzene by reaction with the metal organic compound. The metalated dialkoxybenzene is carbonated and acidified to form the dialkoxybenzoic acid. The preparation of the metal organics, conventionally by reaction of alkali metal with the corresponding organic chloride, uses two mols of alkali metal for each mol of metalated dialkoxybenzene produced overall.

BRIEF DESCRIPTION OF THE INVENTION

It is an object of this invention to provide a method for making dialkoxybenzoic acid comprising the metalation of 1,3-dialkoxybenzene by reaction with potassium dialkylamide.

In accordance with this invention, potassium dialkylamide and 1,3-dialkoxybenzene are contacted in the presence of a tertiary amine solvent, whereby the dialkoxybenzene is metalated, and the reaction mixture is carbonated and acidified in a conventional manner to precipitate the dialkoxybenzoic acid. The potassium dialkylamide may be preformed in the tertiary amine solvent by reaction of substantially equimolar quantities of potassium and dialkylamide with an electron acceptor reactive with potassium, such as α-methylstyrene.

The reaction of the invention is represented by the following equations:

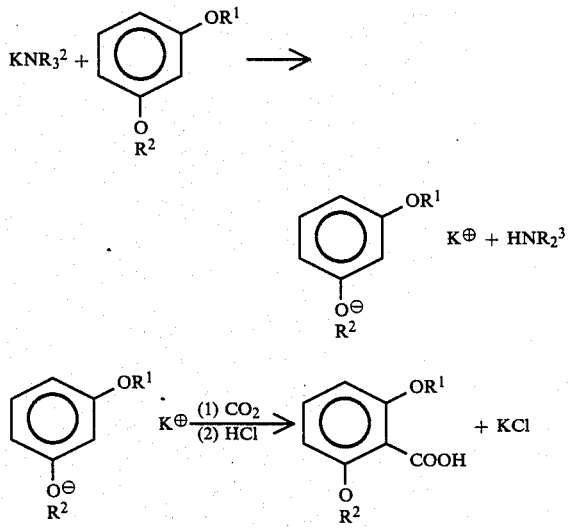

where $R^1$ and $R^2$ are independently a lower alkyl radical, suitably containing up to five C atoms and $R^3$ is a lower alkyl radical or cycloalkyl radical containing up to six C atoms. The dialkylamide, $KNR_2^3$, may be formed by the known reaction of a dispersion of molten potassium with the appropriate dialkylamine and an electron acceptor reactive with potassium to form a free radical intermediate, such as for example, styrene, α-methyl styrene, diisopropenyl benzene or biphenyl, or a fused ring aromatic compound having from 2 to 5 fused rings with or without substituent alkyl groups, such as, for example, naphthalene, phenanthrene, anthracene, acenaphthene, fluorene and pyrene. A substantially stoichiometric amount of electron acceptor is used; that is, one-half the molar quantity of potassium. If the electron acceptor is polymerizable, such as methyl styrene, excess of stoichiometric is to be avoided. The reaction produces one mol of dialkylamide for each mol of potassium, which in turn in accordance with equation 1 and 2 above, reacts with 1 mol of 1,3-dialkoxylbenzene. The reaction mixtures can be used directly in the metalation of 1,3-dialkoxybenzene without the need to separate the potassium dialkylamide.

The reaction is preferably carried out in a tertiary amine solvent, suitably a trialkylamine, cyclic amine or tetraalkylethylene-diamine or mixtures thereof, such as, for example, triethylamine, tetramethylethylenediamine, or 1-methylpyrollidine.

The reaction proceeds readily at slightly elevated temperatures, suitably 25°–80° C. Temperatures above about 100° C. should be avoided to avoid decreased yield and reaction rates are considerably slower at temperatures below room temperature.

The following examples are illustrative of the invention and the best mode presently known for practicing the invention.

EXAMPLE 1

Potassium diethylamide was prepared in a nitrogen-blanketed, 500 ml-Morton flask, equipped with a mechanical stirrer, thermometer, reflux condenser and a 60 ml. pressure equalizing funnel. To 3.75 g. of potassium in the flask was added triethylamine (140 ml.), diethylamine (10 ml.) and three drops of chlorobenzene, a potassium dispersing reagent. The potassium was dispensed at 70° C. and a solution of α-methylstyrene (5.67 g.) in triethylamine was added through the addition funnel over a period of 25 minutes and stirred for 15 minutes after the addition. The mixture was allowed to cool to room temperature.

A solution of 1,3-dimethoxybenzene (12.06 g.) and tetramethylethylenediamine (15 ml.) in triethylamine (20 ml.) was added to the potassium diethylamide reaction mixture and stirred for two hours. The entire mixture, a gray suspension, was poured into a 1-liter beaker containing crushed dry ice (456 g.) with the aid of 35 ml of added triethylamine and was allowed to warm to room temperature. The contents of the beaker were transferred into a 1-liter flask with the aid of some water. All volatile components were removed by a rotary evaporator. The solid remaining in the flask was partitioned between diethyl ether (30 ml.) and water, which was extracted with diethyl ether (four times, 30 ml.). The aqueous layer was acidified with concentrated hydrochloric acid to a pH of 1. The resultant precipitate was collected by filtration, water-washed and air dried to give 10.99 g. (69% yield) of 2,6-dimethoxybenzoic acid.

EXAMPLE 2

Potassium diethylamide was prepared as in Example 1 using 3.82 g. of potassium, 10 ml of diethylamine, 140 ml of triethylamine, a solution of 5.77 g. α-methylstyrene in 20 ml. triethylamine and a drop of chlorobenzene. The reaction mixture was maintained at 70° C. and a solution of 1,3-dimethoxybenzene (5.40 g.) in triethylamine (20 ml) was added to it and stirred at 70° C. for three hours. The reaction mixture was carbonated and acidified as in example 1 yielding 6.05 g. (85% yield) of 2,6-dimethoxybenzoic acid.

I claim:

1. A method of preparing 2,6-dialkoxybenzoic acid comprising the step of metalating 1,3-dialkoxybenzene by reaction of 1,3-dialkoxybenzene where each alkoxy group independently contains up to 5 carbon atoms, with a potassium dialkylamide, in which each alkyl group is a lower alkyl group or cycloalkyl group containing up to six carbon atoms.

2. A method of claim 1 in which the metalated dialkoxybenzene is treated with carbon dioxide and an acid to form 2,6-dialkoybenzoic acid.

3. A method of claim 1 comprising reacting 1,3-dimethoxybenzene and potassium diethylamide.

* * * * *